(12) United States Patent
Bean et al.

(10) Patent No.: US 9,829,310 B2
(45) Date of Patent: Nov. 28, 2017

(54) INTERFEROMETRIC ROLL-OFF MEASUREMENT USING A STATIC FRINGE PATTERN

(71) Applicant: Corning Incorporated, Corning, NY (US)

(72) Inventors: Alexander Timothy Bean, Pittsford, NY (US); Thomas James Dunn, Penfield, NY (US); Christopher Alan Lee, Pittsford, NY (US); Mark Joseph Tronolone, Estero, FL (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 15/198,661

(22) Filed: Jun. 30, 2016

(65) Prior Publication Data
US 2017/0003120 A1    Jan. 5, 2017

Related U.S. Application Data

(60) Provisional application No. 62/186,701, filed on Jun. 30, 2015.

(51) Int. Cl.
*G01B 11/24* (2006.01)
*G01N 21/95* (2006.01)
(Continued)

(52) U.S. Cl.
CPC ...... *G01B 11/2441* (2013.01); *G01B 9/02044* (2013.01); *G01N 21/9503* (2013.01);
(Continued)

(58) Field of Classification Search
CPC .. G01B 11/24; G01B 11/2441; G01B 9/02049
See application file for complete search history.

(56) References Cited

U.S. PATENT DOCUMENTS 6,359,692 B1   3/2002  de Groot
6,449,048 B1   9/2002  Olszak
(Continued)

FOREIGN PATENT DOCUMENTS

JP   2008216099 A   9/2008
JP   2014157106 A   8/2014

OTHER PUBLICATIONS

PCT International Searching Authority; International Search Report and Written Opinion; Application No. PCT/US2016/039712; International Filing Date Jun. 28, 2016; dated Oct. 21, 2016; pp. 1-13.

*Primary Examiner* — Jonathan Hansen
(74) *Attorney, Agent, or Firm* — John P. Ciccarelli

(57) ABSTRACT

An apparatus for measuring the surface contour of a target area of a substrate has a light source to emit a measurement light beam. A beam splitting element defines a measurement axis and a reference axis. A substrate holder disposes the target area along the measurement axis and tilted away from normal incidence, about a tilt axis that orthogonally intersects the measurement axis, according to a predetermined tilt angle that is a function of the measurement light beam wavelength. An imaging sensor records a fringe pattern generated from the measurement light beam and a reference light beam. A computer extracts frequency profiles from the recorded fringe pattern, each profile taken in a direction that is orthogonal to the direction of the tilt axis, wherein the programmed instructions further compute changes in the contour of the target area surface according to the frequency profiles.

20 Claims, 9 Drawing Sheets

(51) Int. Cl.
   *G01B 9/02*    (2006.01)
   *G06T 7/00*    (2017.01)
   *G06T 7/64*    (2017.01)
(52) U.S. Cl.
   CPC .............. *G06T 7/0006* (2013.01); *G06T 7/64*
              (2017.01); *G06T 2207/30148* (2013.01)

(56) References Cited

U.S. PATENT DOCUMENTS

| | | |
|---|---|---|
| 7,209,499 B2 | 4/2007 | Farmiga et al. |
| 7,259,860 B2 | 8/2007 | Marron et al. |
| 7,268,887 B2 | 9/2007 | Kulawiec et al. |
| 7,268,889 B2 | 9/2007 | Kulawiec et al. |
| 7,286,238 B2 | 10/2007 | Lee et al. |
| 7,388,675 B2 | 6/2008 | Indars et al. |
| 7,916,763 B2 | 3/2011 | Dunn et al. |
| 7,986,414 B2 | 7/2011 | Lee et al. |
| 8,218,586 B2 | 7/2012 | Dunn et al. |
| 8,531,677 B2 | 9/2013 | Dunn et al. |
| 2006/0233205 A1 | 10/2006 | Farmiga et al. |
| 2009/0153821 A1* | 6/2009 | Magnusson ......... G03F 7/70066 355/53 |
| 2011/0032503 A1 | 2/2011 | Sasaki |
| 2015/0276375 A1* | 10/2015 | Liu ...................... G01B 9/0203 356/511 |

\* cited by examiner

INTERFEROMETRIC ROLL-OFF MEASUREMENT USING A STATIC FRINGE PATTERN

This application claims the benefit of priority under 35 U.S.C. §119 of U.S. Provisional Application Ser. No. 62/186,701 filed on Jun. 30, 2015, the content of which is relied upon and incorporated herein by reference in its entirety.

FIELD

The disclosure relates generally to optical metrology apparatus and methods and more particularly to apparatus and methods for measurement and characterization of surface profiles such as edge profiles for semiconductor wafers.

BACKGROUND

A number of applications in microelectronics lithography, optics, and other fields benefit from highly accurate surface characterization of a substrate with respect to flatness, edge roll-off, uniformity, axial runout, and other dimensional features. There is particular interest in surface dimensional characterization, to sub-micron accuracy, in applications such as semiconductor wafer preparation and processing.

A familiar metric to those skilled in semiconductor wafer preparation and handling relates to a measurement called Roll-Off Amount (ROA), or referred to as linear roll-off amount (L-ROA), that relates to the edges of the wafer. Successful lithographic processing of the semiconductor wafer can be highly dependent on aspects of the mechanical profile near the edge of the polished wafer. Wafer manufacturers endeavor to accurately characterize and carefully control the wafer profile at the edge in order to meet stringent customer requirements. Industry-accepted ROA standards of measurement are defined, for example, by Semiconductor Equipment and Materials International (SEMI) as SEMI standard M69-0307.

The ROA measurement profiles the flatness characteristic in the region near the edge of the wafer and helps to identify flatness problems caused by polishing errors. The conventional measurement for ROA is typically performed using a stylus or a single point optical probe. The edge of the generally circular wafer is measured at eight different radial angles, typically every 45 degrees around the circumference, in a time-consuming and error-fraught process that can require costly equipment and highly trained technicians.

Interferometric techniques have been used to address the problem of surface edge profile characterization, but with somewhat disappointing results. For example, applying conventional phase-difference interferometric approaches requires dedicated measurement apparatus that holds the sample and reference surfaces in a highly rigid relationship and is well-buffered from vibration. Typical phase measurement algorithms acquire a number of interferograms, with precise equipment adjustment for change of phase between each image acquisition, and with this process repeated at multiple angular increments along the wafer edges. Given the number of steps required, the demanding requirements for precision and vibration protection for the measurement system and environment, and overall time that is needed, it can be appreciated that there is room for improvement in surface characterization methods, particularly methods better suited for edge profile characterization techniques for semiconductor wafers and highly flat substrate surfaces.

SUMMARY

According to an embodiment of the present disclosure, there is provided an apparatus for measuring the surface contour of a target area of a substrate, the apparatus includes a light source energizable to emit a measurement light beam and a beam splitting element that defines a measurement axis and a reference axis. The apparatus further includes a substrate holder that disposes the target area of the substrate along the measurement axis and tilted away from normal incidence, about a tilt axis that orthogonally intersects the measurement axis, according to a predetermined tilt angle that is a function of the measurement light beam wavelength. The apparatus also includes an imaging sensor energizable to record a fringe pattern for the target area, the fringe pattern generated from the measurement light beam and a reference light beam from the reference axis. The apparatus further includes a computer in signal communication with the imaging sensor and programmed with instructions to extract a plurality of frequency profiles from the recorded fringe pattern, each profile taken in a direction that is substantially orthogonal to the direction of the tilt axis, and wherein the programmed instructions further compute changes in the contour of the target area surface according to the frequency profiles.

Additional features and advantages will be set forth in the detailed description which follows, and in part will be readily apparent to those skilled in the art from the description or recognized by practicing the embodiments as described in the written description and claims hereof, as well as the appended drawings.

It is to be understood that both the foregoing general description and the following detailed description are merely exemplary, and are intended to provide an overview or framework to understand the nature and character of the claims.

The accompanying drawings are included to provide a further understanding, and are incorporated in and constitute a part of this specification. The drawings illustrate one or more embodiment(s), and together with the description serve to explain principles and operation of the various embodiments.

BRIEF DESCRIPTION OF THE DRAWINGS

The disclosure will be understood more clearly from the following description and from the accompanying figures, given purely by way of non-limiting example, in which.

DETAILED DESCRIPTION

Figure 1:
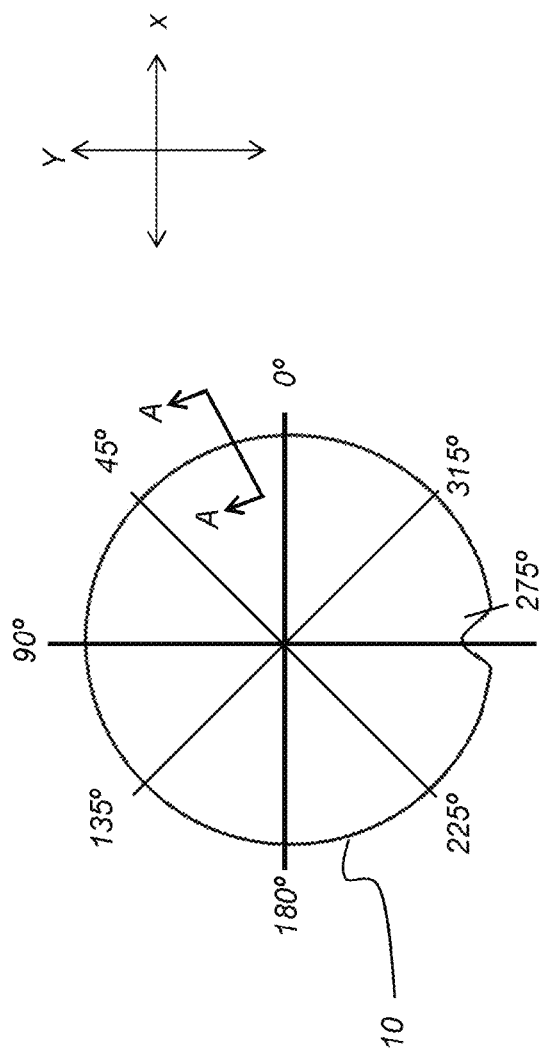
FIG. 1 is a plan view of a semiconductor wafer.

Figures shown and described herein are provided in order to illustrate key principles of operation and fabrication for an optical apparatus according to various embodiments and a number of these figures are not drawn with intent to show actual size or scale. Some exaggeration may be necessary in order to emphasize basic structural relationships or principles of operation.

The figures provided may not show various supporting components, including optical mounts, power sources and circuit board mounting for laser diodes, and other features. It can be appreciated by those skilled in the optical arts that embodiments of the present disclosure can use any of a number of types of standard mounts and support components.

In the context of the present disclosure, terms such as "top" and "bottom" or "above" and "below" or "beneath" are relative and do not indicate any necessary orientation of a component or surface, but are used simply to refer to and distinguish views, opposite surfaces, spatial relationships, or different light paths within a component or apparatus. Similarly, terms "horizontal" and "vertical" may be used relative to the figures, to describe the relative orthogonal relationship of components or light in different planes, for example, but do not indicate any required orientation of components with respect to true horizontal and vertical orientation.

Where they are used, the terms "first", "second", "third", and so on, do not necessarily denote any ordinal or priority relation, but are used for more clearly distinguishing one element or time interval from another. These descriptors are used to clearly distinguish one element from another similar or related element in the context of the present disclosure and claims.

As used herein, the term "energizable" relates to a device or set of components that perform an indicated function upon receiving power and, optionally, upon receiving an enabling signal. For example, a laser diode is energizable to emit a beam of laser light.

In the context of the present disclosure, the term "approximately", when used with reference to a measurement, means within expected tolerances for measurement error and inaccuracy that are accepted in practice. Some reasonable tolerance must be allowed, for example, for measurement differences and for the precision required in a particular application.

Embodiments of the present disclosure describe apparatus and methods for characterization of the edges of a flat substrate and can be used, for example, to provide measured data showing roll-off along edges of a semiconductor substrate or other substrate that is sufficiently specular to allow interferometry measurement. Advantageously, methods and apparatus of the present disclosure can help to provide improvements in speed and measurement accuracy. The interferometric technique described herein has been found to be particularly robust with respect to environmental factors such as vibration and temperature. A single image, obtained at each of a number of angular positions along the periphery of the semiconductor wafer or other substrate to be tested, provides sufficient data for accurate characterization of substrate edges and, more generally, of surface height and height variation. The improved speed enables adding this measurement to existing wafer characterization tools with minimal impact to overall measurement time, even making some types of specialized inspection equipment unnecessary in some cases, which can result in significant savings to the wafer manufacturer.

The plan view of FIG. 1 shows a substrate 10 in the general pattern of a semiconductor wafer to be measured. In conventional testing, measurements are made at each of the positions labeled with angles 0, 45, 90, 135, 180, 225, 275, and 315 degrees. For reference in the description that follows, the plane of the substrate 10 is assigned as the x-y plane.

Figure 2:
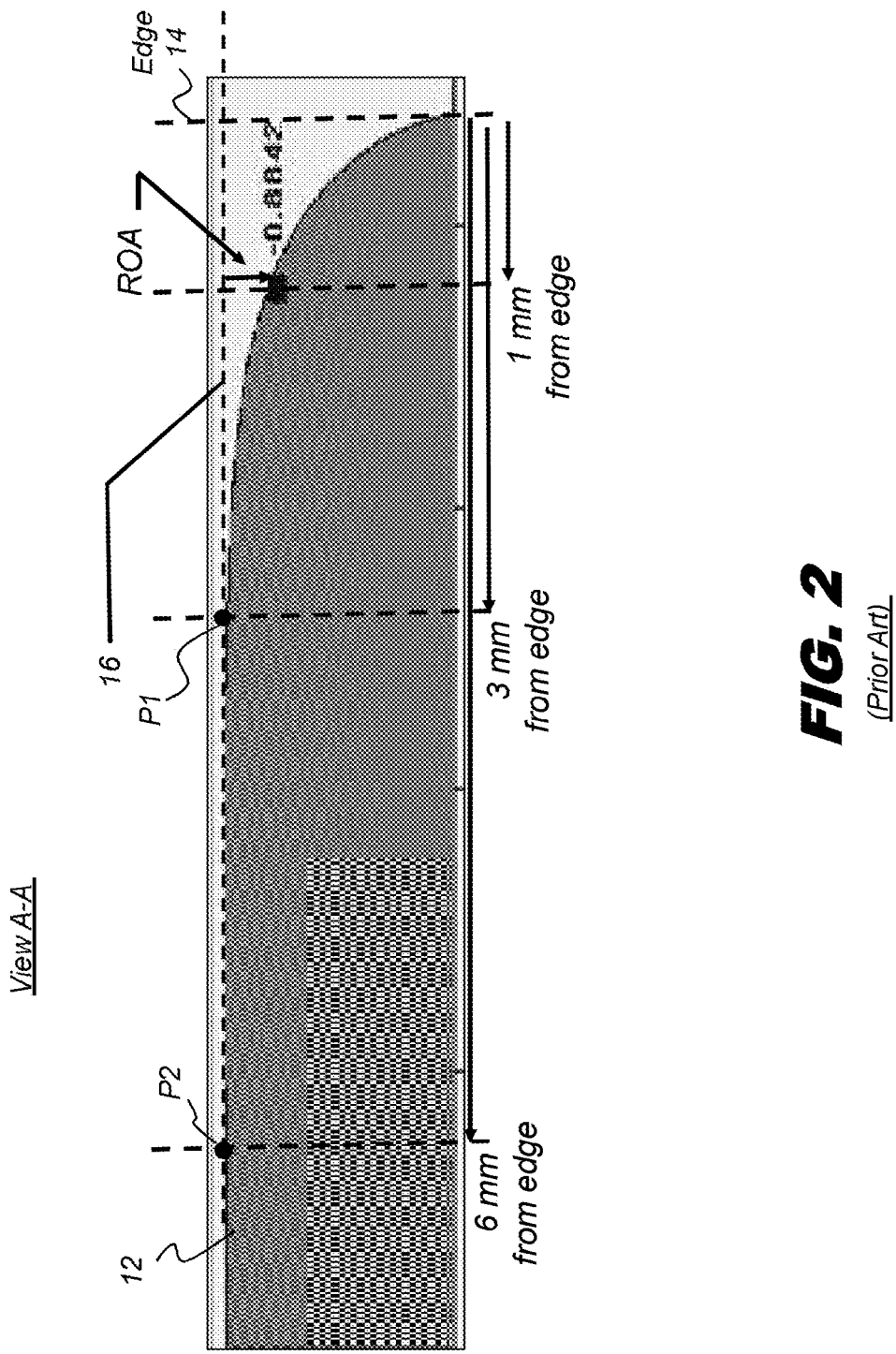
FIG. 2 is a side view that shows edge roll-off for a polished semiconductor wafer.

The cross-sectional side view of FIG. 2 shows a characteristic roll-off curve 12 that can represent ROA along an edge 14, such as along labeled position A-A indicated in FIG. 1. A best-fit line 16 is calculated along the radius of the wafer using two suitable surface points, such as points P1 and P2, respectively 3 mm and 6 mm from edge 14 as shown. Other surface points could be used as a best-fit reference.

Figure 3A:
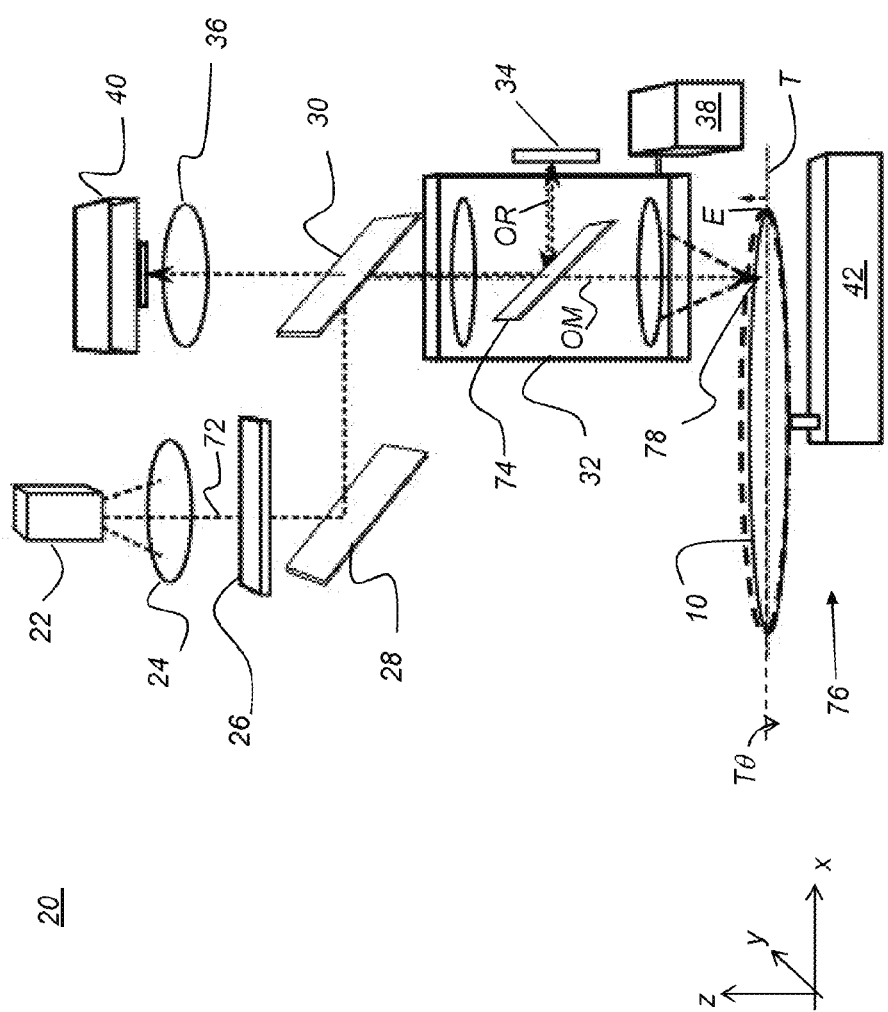
FIG. 3A is a schematic side view that shows components of an optical apparatus for edge roll-off characterization according to an embodiment of the present disclosure.
Figure 3B:
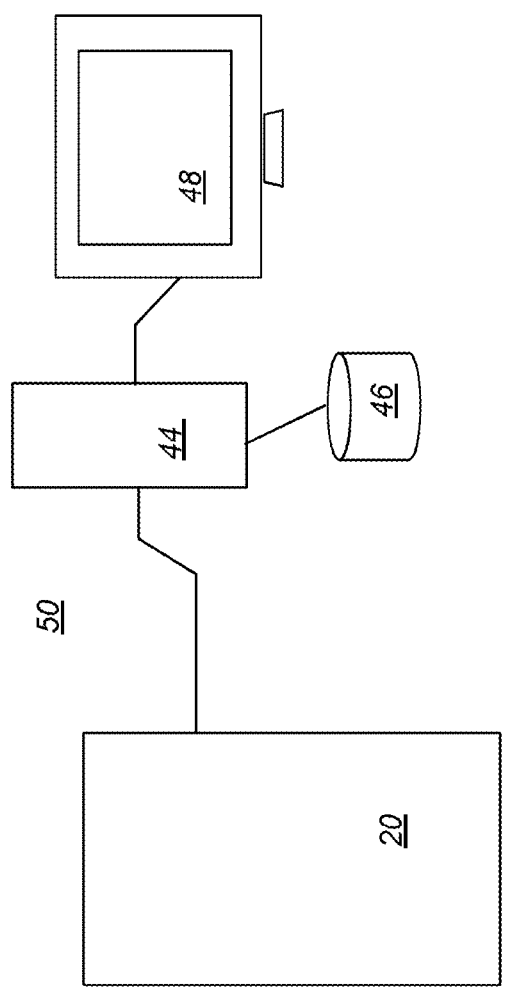
FIG. 3B is a schematic side view that shows a system for edge roll-off characterization according to an embodiment of the present disclosure.

FIG. 3A shows an optical apparatus 20 used for edge characterization of a flat substrate 10 such as a semiconductor wafer, according to an embodiment of the present disclosure. FIG. 3B shows a metrology system 50 that provides control and reporting of the wafer edge characterization process.

In the FIG. 3A arrangement, a broadband light emitting diode (LED) is used as a light source 22, providing light energy that is distributed over a predefined spectral range. According to an embodiment of the present disclosure, a red LED is used, energizable to emit a measurement light beam 72 over the spectral region centered at 635 nm. This broadband source illumination is collimated, such as by one or more lenses as represented by lens 24, and optionally filtered at a spectral filter 26 to obtain the desired optical bandwidth, suited to the desired coherence length, for example. The light is directed by a turning mirror 28 to a beam splitter 30. Beam splitter 30 directs the source illumination to an interferometer 32, such as to an interferometric objective, and to substrate 10. An interferometric objective for interferometer 32 can be, for example, a Michelson interferometric objective or, alternately, a Mirau objective. This type of objective lens includes focusing optics as well as an internal beam splitting element 74 and a reference surface 34 for generation of interferometric fringes. Reference x, y, and z axes are shown.

In the FIG. 3A arrangement, beam splitting element 74 defines a measurement axis OM for measurement light beam 72 and a reference axis OR for a reference light beam. The interferometric objective is oriented above a rotary vacuum spindle or other actuator 42 which acts as a substrate holder 76 and holds the wafer or other substrate 10 for measurement. Interferometer 32 focuses the source illumination onto a target area 78, such as an edge portion of substrate 10 for measuring roll-off. Light returned from target area 78 on the substrate 10 surface and reference light from reference surface 34 then transmits through beam splitter 30 and through one or more lenses 36 and combine to form a fringe pattern that is recorded at an imaging sensor 40, such as a camera. An optional focus adjustment apparatus 38 provides sensing and actuation components for adjusting the focus of the interferometric objective or corresponding optics of interferometer 32 to compensate for changes in surface height, such as from axial runout, as described in more detail subsequently.

The surface of substrate 10 is at a near-normal orientation relative to the measurement axis OM defined by interferometer 32, but is not orthogonal to axis OM. Substrate 10 is tilted slightly at a tilt angle Tθ about an axis T that is in the plane of the substrate 10 surface and can be substantially normal to an edge E of substrate 10 as shown in FIG. 3A. Tilt axis T is orthogonal to measurement axis OM.

The tilt arrangement described with reference to FIG. 3A provides a dense pattern of fringes that are perceived to extend in a direction that is substantially parallel to tilt axis T. The tilt angle Tθ for substrate 10 about tilt axis T is predetermined according to factors that include the wavelength λ of the measurement light beam 72, the pixel resolution of imaging sensor 40, and the number of fringes desired in the image that is obtained.

According to an embodiment of the present disclosure, the tilt angle can be computed using:

$$T\theta = \tan^{-1}\left(\frac{\frac{\lambda}{2}*(Y \text{ pixels of sensor})}{FOV_y * P}\right) \quad (1)$$

wherein P is the number of pixels per fringe in the obtained image; $FOV_y$ is the y dimension of the field of view for imaging sensor 40. By way of example, and not by limitation, for a desired P value of 8 pixels per fringe in a sensor 40 with 1000 pixels in the Y direction and $FOV_y$ of 5 mm, with a wavelength λ of 600 nm, the tilt angle Tθ is approximately 0.43 degrees. An increased wavelength λ increases the tilt angle. The P value is selected for a desired level of contrast and resolution in fringe clarity. Decreasing the desired P value increases the tilt angle.

The tilt angle Tθ itself determines how many fringes are formed for analysis in the interferometric image that is captured, as described in more detail subsequently.

FIG. 3B shows a simplified schematic of a metrology system 50 that uses optical apparatus 20 of FIG. 3A for edge characterization of semiconductor wafers and for surface characterization of other substantially transparent flat substrates as well as curved surfaces. Components of optical apparatus 20 are in signal communication with a computer 44 that is configured as a processor for acquiring each image having interference fringes formed from the combined light reflected from near the edges of the substrate 10 at various angular interval, and the light reflected from reference surface 34 within the interferometric objective or, more generally, the reference light beam. Computer 44 then processes the image results, analyzing the acquired images from the combined light to calculate a carrier frequency according to fringes obtained from along a flat portion of the substrate and comparing fringes obtained from along the flat portion of the substrate with fringes representative of the edge portions of the substrate to determine the phase difference between fringe patterns over the edge portion of the wafer surface being measured. The adjacent fringes are perceived to extend in or along the general direction of the tilt axis T, as noted previously. Computer 44 calculates edge roll-off according to the calculated carrier frequency and phase differences in the fringe pattern that is obtained along the edge portions of the substrate. Computer 44 is in signal communication with a display 48 for displaying results of the edge roll-off calculation and with a memory 46 for storing calculation results. Computer 44 can be a networked computer for transmitting results over a network to a different computer processor for further computation or storage.

Figure 3C:
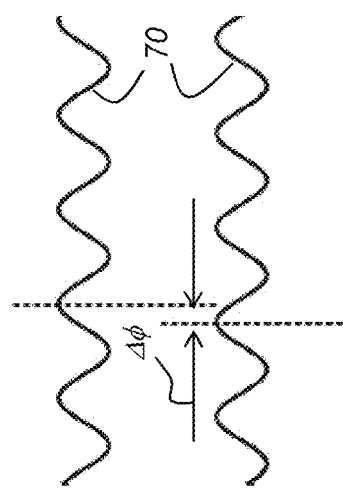
FIG. 3C shows exemplary carrier waves acquired from the fringe pattern captured by the camera or other imaging sensor in the FIG. 3A configuration.

FIG. 3C shows two exemplary carrier waves 70 acquired from the fringe pattern captured by the camera or other imaging sensor 40 in the FIG. 3A configuration. Each carrier wave 70 is obtained from the portion of the fringe pattern that corresponds to a different portion of the measured surface, allowing calculation to determine surface height differences. The phase difference Δϕ relates to the surface height difference, as described in more detail subsequently.

As described with reference to FIG. 3A, a broadband source such as a red LED can be used and has advantages of low cost, low energy, and offers plenty of light. A laser light source would have too much coherence (that is, excessive coherence length) and tend to generate speckle that would degrade the measurement of the wafer profile. In addition, a light source that is highly coherent could generate two sets of interference patterns from opposed surfaces of a thin, transparent substrate such as a sapphire wafer. The incoherent light is collected by an imaging system that images the light to the entrance pupil of the microscope objective through beam splitter 30. This illumination arrangement is known as Kohler illumination and provides a uniform illumination field that maximizes the efficiency of illumination. The illumination is passed through a beam splitter in order to allow the return light to be imaged directly to the camera or other imaging sensor 40. The interferometric objective that provides interferometer 32 can have a field of view that is roughly 10 mm in order to measure the wafer profile over a 10 mm distance.

Figure 4A:
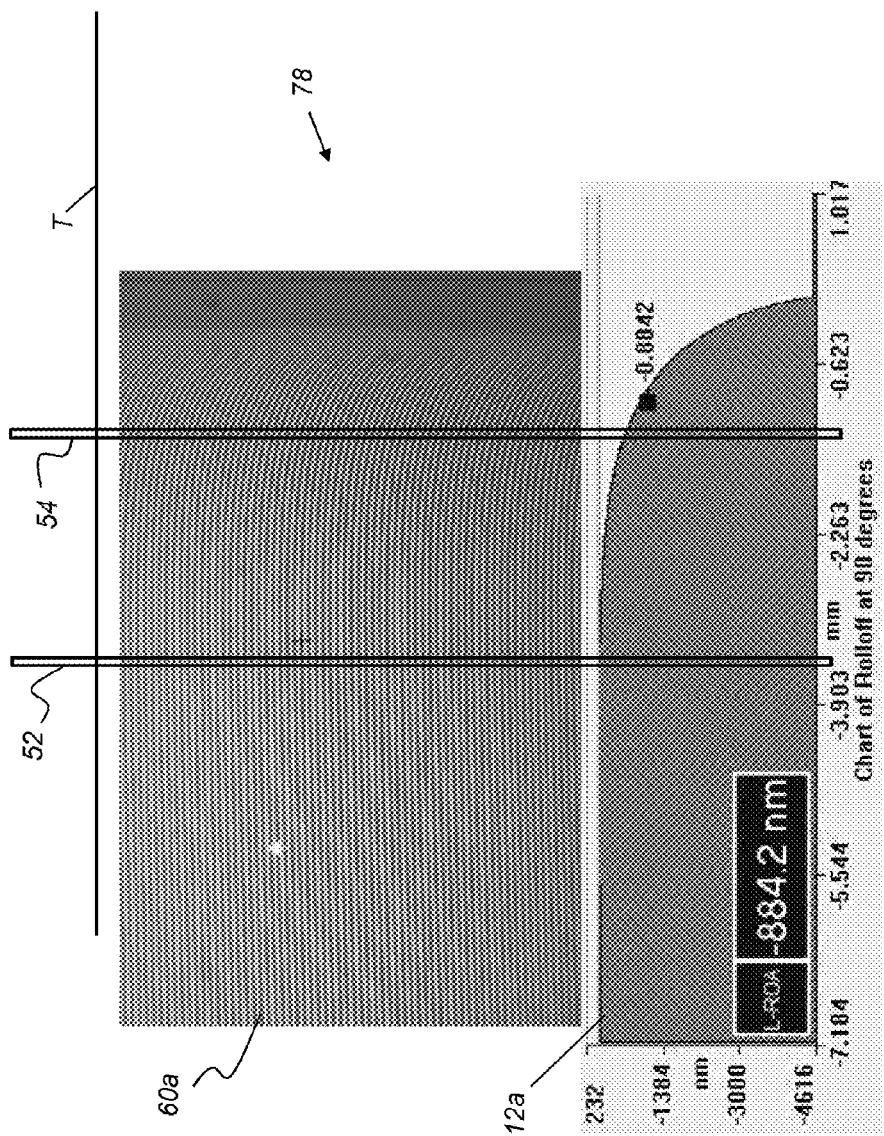
FIG. 4A is an exemplary diagram that relates interference fringes to roll-off measurement.
Figure 4B:
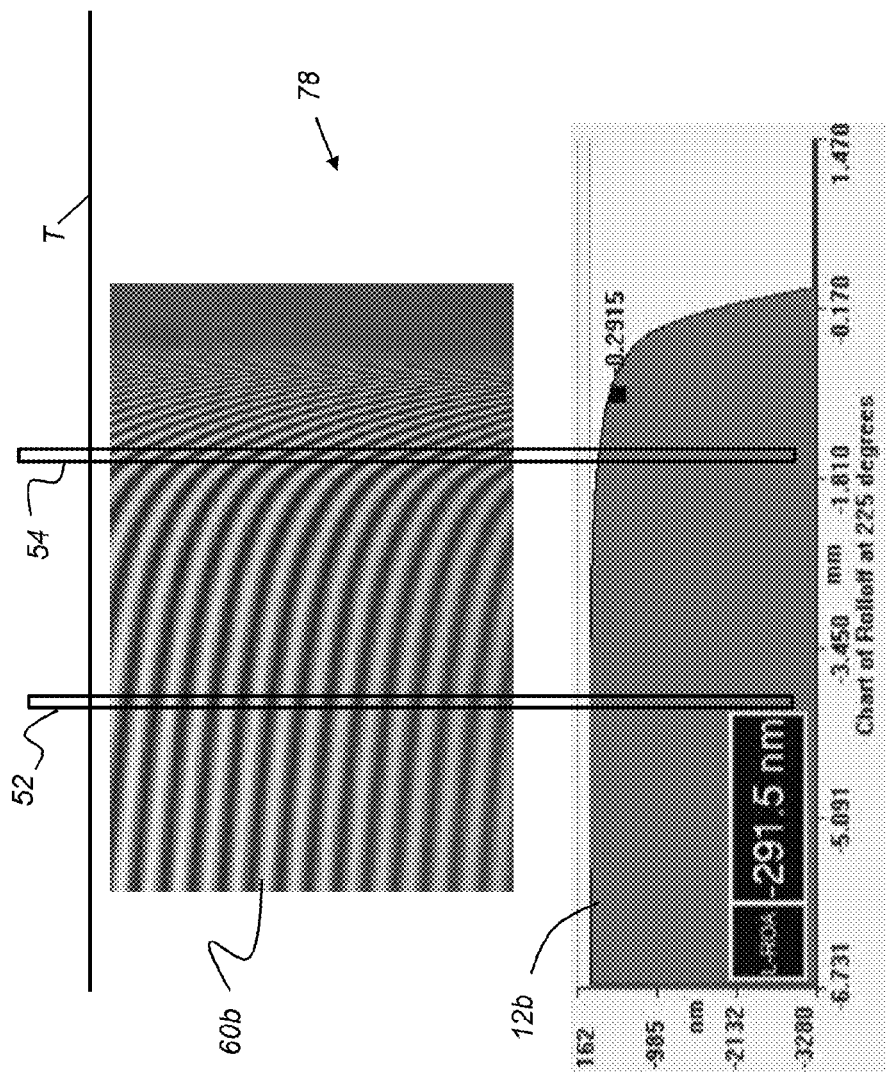
FIG. 4B is another exemplary diagram that relates interference fringes to roll-off measurement.

By way of example, FIG. 4A shows a portion of an image 60a of target area 78 acquired by imaging sensor 40 showing interferometric fringes and relating the fringe pattern to a roll-off curve 12a. In the image orientation shown for image 60a and roll-off characteristic curve 12a, fringes extend along a direction that is substantially parallel to tilt axis T, which has the relative orientation represented in FIG. 4A. FIG. 4B shows another example fringe pattern in an image 60b with a curve 12b showing more pronounced roll-off in target area 78.

Exemplary vertical slices 52 and 54 shown in FIGS. 4A and 4B indicate the direction in which the acquired images are analyzed for frequency content in order to identify phase differences that correspond to height differences. That is, the frequency content of the fringe pattern is analyzed from vertical slices, taken orthogonally with respect to the direction in which the fringes extend (that is, taken orthogonal to tilt axis T). According to an embodiment of the present disclosure, Fourier analysis is used to interpret the fringe pattern as representative of an edge profile in roll-off curve 12. In the particular example of FIGS. 4A and 4B, slice 52 is taken over an essentially flat portion of the substrate surface. Slice 54 is representative of changes in the fringe pattern for fringes near the edge of the substrate surface, where roll-off is observed. In practice, multiple slices are obtained and analyzed for carrier wave phase information that can provide highly accurate characterization of the substrate edge. It can be appreciated that any suitable sampling interval between successively analyzed vertical slices such as slices 52 and 54 can be used for plotting the roll-off profile, as shown in the examples of FIGS. 4A and 4B.

It should be noted that the wafer or other substrate 10 is tilted along axis T as described previously with reference to FIG. 3A, at least slightly tilted at an oblique angle with respect to the optical axis, measurement axis OM. The slight tilt is used to form a carrier fringe pattern which is used to calculate the near edge wafer geometry. The overall tilt configuration also enables the system to tolerate physical displacement or thickness deviation of the wafer surface, and still be able to generate fringes even with a short coherence light source.

It can be appreciated that, unlike a number of conventional surface characterization techniques, the apparatus and methods of the present disclosure allow a portion of the surface of a wafer or other substrate to be characterized using a fringe pattern that is captured in a single image frame, as is shown in images 60a and 60b of FIGS. 4A and 4B respectively. To take advantage of the pixel resolution that is available, the camera or other type of imaging sensor 40 can be aligned with the fringe pattern, such as by alignment of the image sensing array within the camera to the tilt axis T used for substrate 10. With precise alignment of the camera or other type of imaging sensor 40 to the tilted substrate 10, each of vertical slices 52 and 54 corresponds to a column of pixels for the camera or other imaging sensor array. The analyzed slices, such as slices 52 and 54, are taken substantially orthogonal to the direction of fringes, such as within approximately +/−4 degrees or less of orthogonal over the extent of the fringes; slices 52 and 54 can be taken at other angles, but using a substantially orthogonal orientation simplifies subsequent computation, particularly when slices 54 and 52 align with columns of pixels on imaging sensor 40 (FIG. 3A). This capability for localized surface characterization, using image-sized "tiles" such as those described herein with reference to FIGS. 4A and 4B, can be advantageous for providing an edge profile for a substrate as well as for providing surface measurements for any of a number of types of flat or curved or irregularly contoured surfaces that exhibit sufficient reflection of the incident measurement beam to generate perceptible fringes. This method can be applied for use with substrates that are opaque or transparent. Light sources and filters used to determine bandwidth can be adjusted to optimize measurement results for the particular substrate that is examined.

For semiconductor wafer profiling, for example, the generated fringe pattern is analyzed to create a sub-field trace that extends radially toward the edge of the wafer, thereby examining the edge contour at one location along the perimeter of the wafer in a single camera frame; this eliminates the need for full scanning of the wafer. In addition, this approach allows a measurement that is relatively robust to vibration, since the data acquisition time can be extremely short, on the order of a few milliseconds, for example. The resulting robustness to vibration allows increased accuracy and reduced environmental sensitivity when compared against conventional scanning methods. Extremely fast data collection allows for measurement of the wafer even while moving, provided that image resolution and quality are not compromised. This feature helps to further enhance the speed of measurement and analysis over conventional methods.

As shown in FIGS. 4A and 4B, interferometric fringes result with the wafer illuminated as it is tilted slightly in the vertical direction. A series of fringes appear, horizontal in the orientation of FIGS. 60a and 60b, and can be aligned with the pixel array data captured by camera or other type of imaging sensor 40. Embodiments of the present disclosure thus plot the intensity variation along a vertical column of pixels from the camera to obtain a sinusoidal intensity pattern of a particular spatial frequency. This spatial frequency acts as a carrier wave that allows the phase measurement to indicate the wafer height along the horizontal axis that is parallel to the tilt axis T in the acquired image.

Given the carrier wave data obtained from the captured image, it is possible to obtain, at each of a succession of one-dimensional slices of the image taken orthogonally to the fringe length direction, the phase of the carrier wave. A straightforward Fourier transform operation can be readily performed on the vertical one-dimensional array of intensity data. The phase ($\phi$) can be converted into height information (h) using the simple relation:

$$h = \frac{p}{2\pi} * \frac{\lambda}{2} \quad (2)$$

wherein $\lambda$ is the wavelength of the illuminating radiation from light source 22 (FIG. 3A). By measuring the phase of each vertical column of camera pixels from the acquired image, and comparing phase changes $\Delta\phi$ along the horizontal (length) of the image a profile can be obtained across the horizontal axis.

Figure 5:
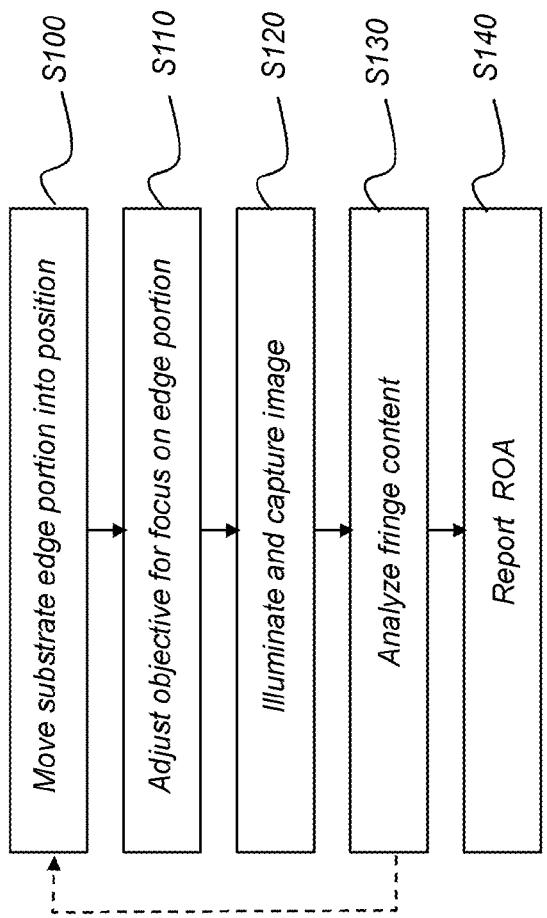
FIG. 5 is a logic flow diagram that shows a sequence for edge roll-off data acquisition and processing.

The logic flow diagram of FIG. 5 shows a sequence of steps that can be used with the system shown in FIGS. 3A and 3B to characterize edge roll-off for a semiconductor wafer or, more generally, to characterize a portion of a substrate surface, such as a flat or curved substrate, measuring the surface contour of a target area according to an embodiment of the present disclosure. In a positioning step S100, the wafer or other substrate 10 is positioned for imaging by camera or other type of imaging sensor 40. Positioning step S100 typically rotates the substrate 10 into position so that a portion of the edge of the substrate 10 lies within the camera's object field. Step S100 can be performed manually or can be controlled from a user interface display or according to a stored program of instructions that allow automated inspection of surfaces in a pre-programmed pattern. Thus, for example, with respect to FIG. 3B, computer 44 or other control logic processor can provide control instructions for operation of metrology system 50, including control of operation of optical apparatus 20 components such as substrate positioning, tilt, and focus.

Figure 6:
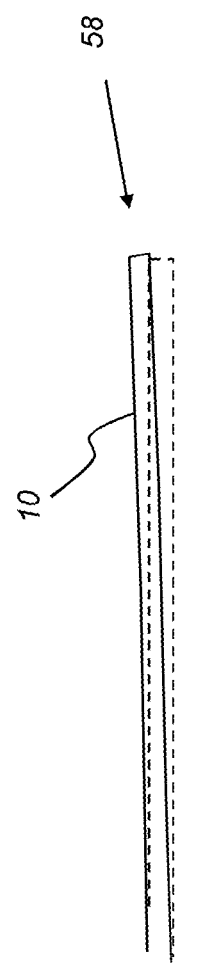
FIG. 6 is a side view showing axial runout.

Continuing with the FIG. 5 sequence, a focus adjustment step S110 adjusts focus of the objective of interferometer 32 to compensate for inadvertent movement as well as for axial runout 58, as shown in exaggerated form in FIG. 6, due to imperfect flatness of the surface. As FIG. 6 shows, there is typically some amount of axial runout 58 that causes the desired measurement area to move up and down as the wafer is rotated. This can come from flatness errors of the wafer or from the plane of the wafer chuck not being orthogonal to the rotational axis. The amount of axial runout can range from a few microns to a few millimeters. The amount of axial runout is an important consideration in the design of a system for measuring wafer edge profiles. Image contrast can be used to detect conditions that necessitate focus adjustment and can provide this information to adjustment components for automation of the adjustment.

Continuing with FIG. 5, an image acquisition step S120 then executes, in which light source 22 is energized and the light used to generate a fringe pattern for capture by camera or other type of imaging sensor 40. The captured image is then ready for storage in memory and an image analysis step S130 is performed to determine frequency content. For this processing, computer 44 can use a Fast-Fourier Transform (FFT) or other type of transform that allows straightforward extraction of frequency data from the fringe pattern. The frequency data can be used to determine the relative amount of roll-off for a given vertical slice of the image, for example. A results display step S140 reports the results of roll-off analysis for one or more of the acquired images. Results can also be stored or transmitted to another computer or other processor, such as a networked processor.

Steps S100, S110, S120, S130, and S140, or a subset of these steps, can be repeated as many times as necessary for the desired characterization of a target area, such as substrate edges. For example, the eight angular locations shown in FIG. 1 can be inspected and imaged, using the process described herein with reference to FIG. 5; however, these steps need not be limited to the eight measurement points conventionally used for edge roll-off characterization.

Other modifications can be applied to the conventional measurement sequence. For example, images can be obtained at increments of every 10 degrees or every 5 degrees or any other interval, allowing more precise characterization to be performed. The use of additional test points can be practical because of the reduced amount of time needed at each angular location. In addition, only a single image needs to be obtained, which is advantageous for robustness to vibration.

Because only a single image frame captures the edge roll-off data, the collection time is reduced to the integration time of one frame. This has a dramatic impact on the total acquisition time and minimizes the impact of vibrations. It also makes it possible to collect data while the substrate is moving, provided the integration time is short enough to capture the surface. With only one frame to analyze the surface, it is not possible to use standard phase measurement algorithms to generate a surface height map of the whole surface. Instead, methods of the present disclosure add tilt interference fringes to effectively introduce a carrier wave and evaluate the surface profile along an axis orthogonal to the tilt direction.

Because the arrangement of FIG. 3A employs an incoherent light source, interferometric fringes are not generated unless the reference arm and measurement arm of the interferometric objective are carefully matched. This means the wafer surface under the interferometric objective must be positioned so that the distance from the wafer surface to the beam splitting element inside of the objective is the same as the reference arm to reference surface 34 in the objective. The allowable mismatch in the two arms of the interferometer is determined by the coherence length of the light source. The coherence length ($\Delta l$) of the light source is related to the bandwidth ($\Delta \lambda$) according to the following formula:

$$\Delta l = 0.44 * \frac{\lambda^2}{\Delta \lambda} \quad (3)$$

where $\lambda$ is the center wavelength from the LED source. There is clear trade-off between the desired coherence length of the source, and the amount of power from the light source that is usable. It is desirable to have a coherence length that is longer than the axial runout of the wafer so that the fringe contrast remains high as the measurement area moves up and down under the interferometric objective. However, reducing the LED bandwidth to increase the coherence length effectively wastes most of the light from the LED source, and would increase the integration time, reducing the advantages that were gained from capturing a single frame.

Implementations of the processes for control of actuators for focus and substrate positioning, for image acquisition, image data processing, frequency signal analysis, and results reporting, transmission, and display for the apparatus and methods described herein may be executed using instructions stored in digital electronic circuitry, or in computer hardware, firmware, or software, or in combinations of hardware and software logic. Algorithm and control logic may implemented as a computer program product, i.e., a computer program tangibly embodied in an information carrier, e.g., in a machine-readable storage device, for execution by, or to control the operation of, data processing apparatus, e.g., a programmable processor, a computer, or multiple computers. A computer program can be written in any form of programming language, including compiled or interpreted languages, and can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network.

Method steps may be performed by one or more programmable processors executing a computer program to perform functions by operating on input data and generating output. Some or all of the method steps also may be performed by, and an apparatus may be implemented as, special purpose logic circuitry, e.g., an FPGA (field programmable gate array) or an ASIC (application-specific integrated circuit).

Processors suitable for the execution of a computer program as control logic processor or computer 44 as described herein include, by way of example, both general and special purpose microprocessors, and any one or more processors of any kind of digital computer. Generally, a processor will receive instructions and data from a non-transitory memory, such as a read-only memory or a random access memory or both. Elements of a computer may include at least one processor for executing instructions and one or more memory devices for storing instructions and data. Generally, a computer also may include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile and/or non-transitory memory, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory may be supplemented by, or incorporated in, special purpose logic circuitry.

To provide for interaction with a user, various embodiments of the present disclosure may be implemented on a computer having a display device, e.g., a cathode ray tube (CRT) or liquid crystal display (LCD) monitor, for displaying information to the user and a keyboard and a pointing device, e.g., a mouse or a touch screen, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. Embodiments may be implemented in a computing system that includes a back-end component, e.g., as a data server, or that includes a middleware component, e.g., an application server, or that includes a front-end component, e.g., a client computer having a graphical user interface or a Web browser through which a user can interact with an implementation, or any combination of such back-end, middleware, or front-end components. Components may be interconnected by any form or medium of digital data communication, e.g., a communication network. Examples of communication networks include a local area network (LAN) and a wide area network (WAN), e.g., the Internet.

According to an aspect (1) of the present disclosure, an apparatus for measuring the surface contour of a target area of a substrate is provided. The apparatus comprises: a light source energizable to emit a measurement light beam; a beam splitting element that defines a measurement axis and a reference axis; a substrate holder that disposes the target area of the substrate along the measurement axis and tilted away from normal incidence, about a tilt axis that orthogonally intersects the measurement axis, according to a predetermined tilt angle that is a function of the measurement light beam wavelength; an imaging sensor energizable to record a fringe pattern for the target area, the fringe pattern generated from the measurement light beam and a reference light beam from the reference axis; and a computer in signal communication with the imaging sensor and programmed with instructions to extract a plurality of frequency profiles from the recorded fringe pattern, each profile taken in a direction that is substantially orthogonal to the direction of the tilt axis, wherein the programmed instructions further compute changes in the contour of the target area surface according to the frequency profiles.

According to another aspect (2) of the present disclosure, the apparatus of aspect (1) is provided wherein the light source is a solid-state light source.

According to another aspect (3) of the present disclosure, the apparatus of any of aspects (1)-(2) is provided wherein the light source is a light emitting diode and further comprising a spectral filter in the path of light from the light source.

According to another aspect (4) of the present disclosure, the apparatus of any of aspects (1)-(3) is provided wherein the substrate holder is further actuable to rotate the substrate for measurement of a plurality of target areas.

According to another aspect (5) of the present disclosure, the apparatus of any of aspects (1)-(4) is provided further comprising an actuator for focus adjustment along the measurement axis.

According to another aspect (6) of the present disclosure, the apparatus of any of aspects (1)-(5) is provided wherein the target area is an edge portion of the substrate.

According to another aspect (7) of the present disclosure, the apparatus of any of aspects (1)-(6) is provided wherein the substrate is flat.

According to another aspect (8) of the present disclosure, the apparatus of any of aspects (1)-(7) is provided wherein the image sensor comprises an array of pixels arranged in rows and columns and wherein the rows are aligned with the tilt axis.

According to another aspect (9) of the present disclosure, the apparatus of any of aspects (1)-(8) is provided wherein the substrate holder rotates the substrate during recording by the imaging sensor.

According to another aspect (10) of the present disclosure, an apparatus for measuring the surface contour of a perimeter portion of a substrate is provided. The apparatus comprises: a light source energizable to emit a measurement light beam; an interferometer having a measurement axis and a reference axis; a substrate holder that disposes the perimeter portion of the substrate along the measurement axis and tilted away from normal incidence, about a tilt axis that orthogonally intersects the measurement axis, wherein the tilt axis is orthogonal to an edge of the perimeter portion, according to a predetermined tilt angle that is a function of the measurement light beam wavelength; an imaging sensor energizable to record a fringe pattern for the perimeter portion of the substrate, the fringe pattern generated from the measurement light beam and a reference light beam from the reference axis; and a computer in signal communication with the imaging sensor and programmed with instructions to extract a carrier wave from the recorded fringe pattern, taken in a direction that is substantially orthogonal to the direction of the tilt axis, wherein the programmed instructions further compute surface contour measurements according to changes in the phase of the carrier wave.

According to another aspect (11) of the present disclosure, the apparatus of aspect (10) is provided wherein the light source is a solid-state light source and further comprising a spectral filter for the emitted light.

According to another aspect (12) of the present disclosure, the apparatus of any of aspects (10)-(11) is provided wherein the interferometer comprises a Michelson objective.

According to another aspect (13) of the present disclosure, the apparatus of any of aspects (10)-(12) is provided wherein the interferometer comprises a Mirau objective.

According to another aspect (14) of the present disclosure, the apparatus of any of aspects (10)-(13) is provided wherein the programmed instructions further display surface contour measurements according to changes in the phase of the carrier wave.

According to another aspect (15) of the present disclosure, a method for measuring the surface contour of a target area of a substrate is provided. The method is executed at least in part by a computer and comprises: energizing a light source to emit a measurement light beam; directing the measurement light beam to an interferometer having a measurement axis and a reference axis; disposing the target area of the substrate along the measurement axis and tilted away from normal incidence, about a tilt axis that orthogonally intersects the measurement axis, according to a predetermined tilt angle that is a function of the measurement light beam wavelength; recording a fringe pattern for the target area, the fringe pattern generated from the measurement light beam and a reference light beam from the reference axis; extracting a plurality of frequency profiles from the recorded fringe pattern, each profile taken in a direction that is substantially orthogonal to the direction of the tilt axis; and computing changes in the contour of the target area surface according to the frequency profiles.

According to another aspect (16) of the present disclosure, the method of aspect (15) is provided further comprising automatically adjusting focus of the interferometer along the measurement axis according to a change in height of the substrate surface.

According to another aspect (17) of the present disclosure, the method of any of aspects (15)-(16) is provided further comprising displaying the contour of the target area surface according to the computed changes.

According to another aspect (18) of the present disclosure, the method of any of aspects (15)-(17) is provided wherein computing changes in the contour comprises applying Fourier analysis to the plurality of extracted frequency profiles.

According to another aspect (19) of the present disclosure, the method of any of aspects (15)-(18) is provided wherein the target area is a first target area and further comprising rotating the substrate to measure a second target area using the same sequence of steps.

According to another aspect (20) of the present disclosure, the method of any of aspects (15)-(19) is provided wherein the target area lies along the perimeter of the substrate.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred.

It will be apparent to those skilled in the art that various modifications and variations can be made without departing from the spirit or scope of the disclosure. Since modifications combinations, sub-combinations and variations of the disclosed embodiments incorporating the spirit and substance of the disclosure may occur to persons skilled in the art, the disclosure should be construed to include everything within the scope of the appended claims and their equivalents.

What is claimed is:

1. An apparatus for measuring the surface contour of a target area of a substrate, the apparatus comprising:
   a light source energizable to emit a measurement light beam;
   a beam splitting element that defines a measurement axis and a reference axis;
   a substrate holder that disposes the target area of the substrate along the measurement axis and tilted away from normal incidence, about a tilt axis that orthogonally intersects the measurement axis, according to a predetermined tilt angle that is a function of the measurement light beam wavelength;
   an imaging sensor energizable to record a fringe pattern for the target area, the fringe pattern generated from the measurement light beam and a reference light beam from the reference axis; and
   a computer in signal communication with the imaging sensor and programmed with instructions to extract a plurality of frequency profiles from the recorded fringe pattern, each profile taken in a direction that is substantially orthogonal to the direction of the tilt axis, wherein the programmed instructions further compute changes in the contour of the target area surface according to the frequency profiles.

2. The apparatus of claim 1 wherein the light source is a solid-state light source.

3. The apparatus of claim 1 wherein the light source is a light emitting diode and further comprising a spectral filter in the path of light from the light source.

4. The apparatus of claim 1 wherein the substrate holder is further actuable to rotate the substrate for measurement of a plurality of target areas.

5. The apparatus of claim 1 further comprising an actuator for focus adjustment along the measurement axis.

6. The apparatus of claim 1 wherein the target area is an edge portion of the substrate.

7. The apparatus of claim 1 wherein the substrate is flat.

8. The apparatus of claim 1 wherein the image sensor comprises an array of pixels arranged in rows and columns and wherein the rows are aligned with the tilt axis.

9. The apparatus of claim 1 wherein the substrate holder rotates the substrate during recording by the imaging sensor.

10. An apparatus for measuring the surface contour of a perimeter portion of a substrate, the apparatus comprising:
    a light source energizable to emit a measurement light beam;
    an interferometer having a measurement axis and a reference axis;
    a substrate holder that disposes the perimeter portion of the substrate along the measurement axis and tilted away from normal incidence, about a tilt axis that orthogonally intersects the measurement axis, wherein the tilt axis is orthogonal to an edge of the perimeter portion, according to a predetermined tilt angle that is a function of the measurement light beam wavelength;
    an imaging sensor energizable to record a fringe pattern for the perimeter portion of the substrate, the fringe pattern generated from the measurement light beam and a reference light beam from the reference axis; and
    a computer in signal communication with the imaging sensor and programmed with instructions to extract a carrier wave from the recorded fringe pattern, taken in a direction that is substantially orthogonal to the direction of the tilt axis, wherein the programmed instructions further compute surface contour measurements according to changes in the phase of the carrier wave.

11. The apparatus of claim 10 wherein the light source is a solid-state light source and further comprising a spectral filter for the emitted light.

12. The apparatus of claim 10 wherein the interferometer comprises a Michelson objective.

13. The apparatus of claim 10 wherein the interferometer comprises a Mirau objective.

14. The apparatus of claim 10 wherein the programmed instructions further display surface contour measurements according to changes in the phase of the carrier wave.

15. A method for measuring the surface contour of a target area of a substrate, the method executed at least in part by a computer and comprising:
    energizing a light source to emit a measurement light beam;
    directing the measurement light beam to an interferometer having a measurement axis and a reference axis;
    disposing the target area of the substrate along the measurement axis and tilted away from normal incidence, about a tilt axis that orthogonally intersects the measurement axis, according to a predetermined tilt angle that is a function of the measurement light beam wavelength;
    recording a fringe pattern for the target area, the fringe pattern generated from the measurement light beam and a reference light beam from the reference axis;
    extracting a plurality of frequency profiles from the recorded fringe pattern, each profile taken in a direction that is substantially orthogonal to the direction of the tilt axis; and
    computing changes in the contour of the target area surface according to the frequency profiles.

16. The method of claim 15 further comprising automatically adjusting focus of the interferometer along the measurement axis according to a change in height of the substrate surface.

17. The method of claim 15 further comprising displaying the contour of the target area surface according to the computed changes.

18. The method of claim 15 wherein computing changes in the contour comprises applying Fourier analysis to the plurality of extracted frequency profiles.

19. The method of claim 15 wherein the target area is a first target area and further comprising rotating the substrate to measure a second target area using the same sequence of steps.

20. The method of claim 15 wherein the target area lies along the perimeter of the substrate.

* * * * *